(12) United States Patent
Ogura

(10) Patent No.: US 9,592,509 B2
(45) Date of Patent: Mar. 14, 2017

(54) FLOW PASSAGE DEVICE AND METHOD OF TRANSPORTING LIQUID USING THE SAME

(75) Inventor: Masaya Ogura, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/985,524

(22) PCT Filed: Jan. 25, 2012

(86) PCT No.: PCT/JP2012/052201
§ 371 (c)(1),
(2), (4) Date: Aug. 14, 2013

(87) PCT Pub. No.: WO2012/111429
PCT Pub. Date: Aug. 23, 2012

(65) Prior Publication Data
US 2013/0319534 A1  Dec. 5, 2013

(30) Foreign Application Priority Data
Feb. 16, 2011  (JP) ................. 2011-031039

(51) Int. Cl.
*B01L 3/00* (2006.01)
*G01N 35/08* (2006.01)
*G01N 27/447* (2006.01)

(52) U.S. Cl.
CPC ......... *B01L 3/561* (2013.01); *B01L 3/502715* (2013.01); *B01L 3/502723* (2013.01); *G01N 27/44756* (2013.01); *G01N 35/08* (2013.01); *B01L 2200/027* (2013.01); *B01L 2200/0684* (2013.01); *B01L 2300/0816* (2013.01); *Y10T 137/0318* (2015.04)

(58) Field of Classification Search
None
See application file for complete search history.

(56) References Cited

U.S. PATENT DOCUMENTS

| 4,756,884 A | 7/1988 | Hillman et al. |
| 2005/0277185 A1* | 12/2005 | Levin ............... B01L 3/5025 435/287.1 |
| 2006/0127277 A1 | 6/2006 | Numajiri |
| 2011/0023635 A1 | 2/2011 | Sukawa |

FOREIGN PATENT DOCUMENTS

| CA | 1275231 C | 10/1990 |
| CN | 102016597 A | 4/2011 |
| EP | 212314 A2 | 3/1987 |
| EP | 2275822 A1 | 1/2011 |
| JP | H6-094722 A | 4/1994 |
| JP | 2005-199231 A | 7/2005 |
| JP | 2006-170654 A | 6/2006 |
| JP | 2008-128906 A | 6/2008 |
| JP | 2008-232655 A | 10/2008 |
| JP | 2010-065584 A | 3/2010 |
| JP | 2010-091440 A | 4/2010 |
| WO | 2009/130977 A1 | 10/2009 |

* cited by examiner

Primary Examiner — Natalia Levkovich
(74) Attorney, Agent, or Firm — Canon U.S.A., Inc. IP Division

(57) ABSTRACT

A flow passage device is provided, with which a liquid is easily introduced and introduction of air bubbles into a flow passage along with a liquid when the liquid is introduced into the flow passage can be decreased.

A flow passage device according to the present invention includes a flow passage through which a fluid flows in a direction different from a vertical direction, an introducing space that has a supply port opening toward the vertical direction and introduces a liquid into the flow passage, and a buffering space that connects the flow passage to the introducing space. The buffering space allows a gas-liquid interface to be formed due to surface tension. A direction in which the gas-liquid interface faces is different from the vertical direction.

13 Claims, 8 Drawing Sheets

NO REMAINING LIQUID IN INTRODUCING SPACE

NO REMAINING LIQUID IN INTRODUCING SPACE

LIQUID MOVES IN VOLUME
d (SECTION OF FLOW PASSAGE) ·
m (MOVEMENT DISTANCE)

LIQUID MOVES IN VOLUME
d (SECTION OF FLOW PASSAGE) ·
m (MOVEMENT DISTANCE)

LIQUID INTRODUCTION AFTER MOVEMENT

LIQUID INTRODUCTION AFTER MOVEMENT

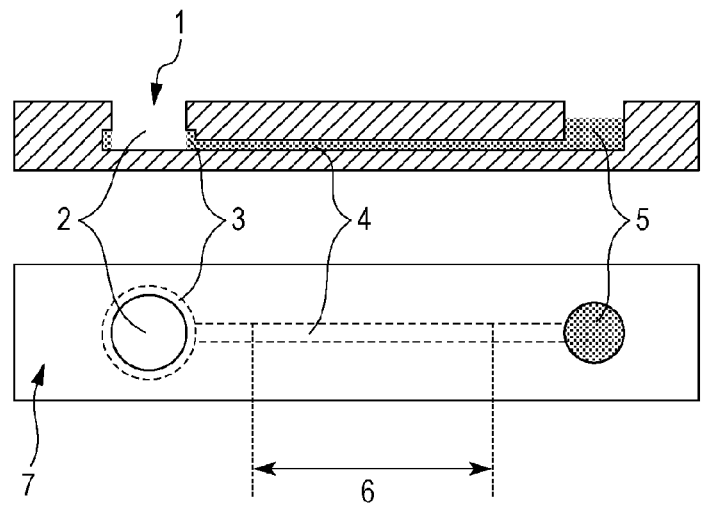

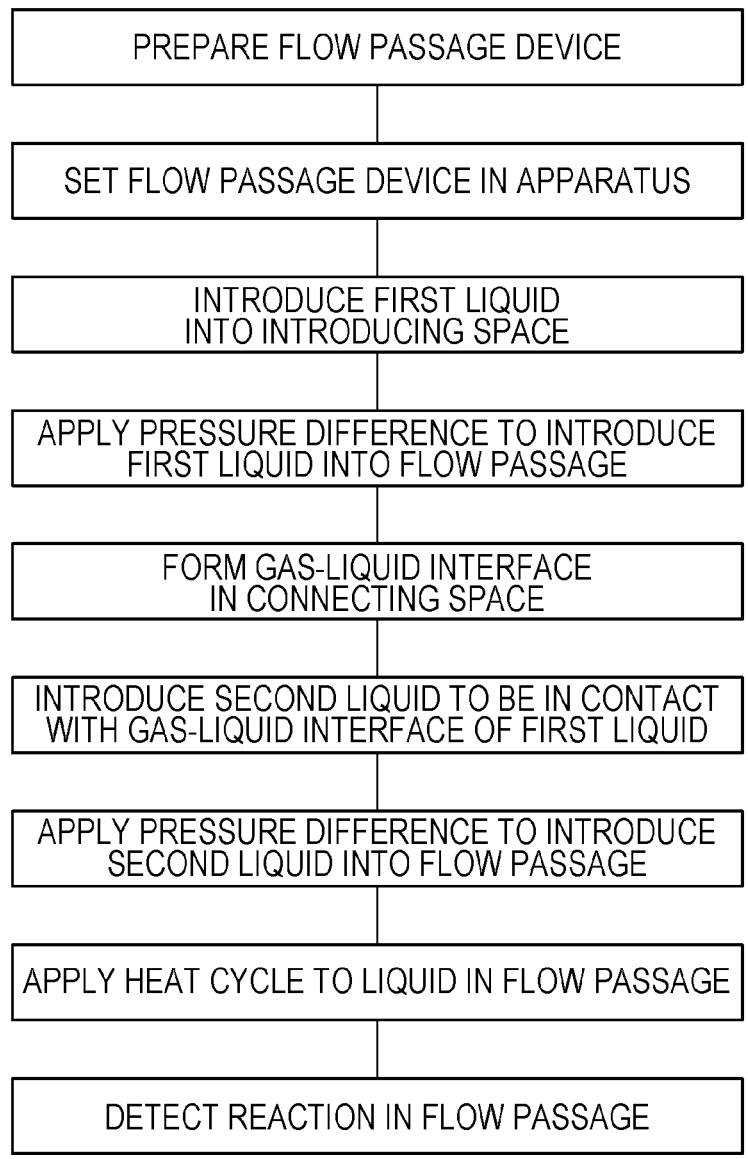

FLOW PASSAGE DEVICE AND METHOD OF TRANSPORTING LIQUID USING THE SAME

TECHNICAL FIELD

The present invention relates to flow passage devices that transport fluids such as specimens, reagents and the like. The flow passage devices according to the present invention are useful as medical testing devices used for medical tests such as genetic tests and protein tests.

BACKGROUND ART

Medical testing devices that use chemical reactions as a main analytical mechanism are being developed. In existing specimen tests, reagents are required for chemical analyses, preparation of reagents, chemical syntheses, and reaction detection on the order of milliliters (ml) to microliters (μl). Such tests performed using test-tubes or the like can now be performed on the order of nanoliters (nl) by formation of a fine reaction field using a litho-process technology and a thick film process technology. The micro total analysis system (μ-TAS) is a technology that utilizes such fine reaction fields. The μ-TAS technology is applicable to fields of genetic testing, chromosomal testing, cell testing and the like used for medical tests and diagnoses, biotechnologies, tests of substances present in very small amounts in the environment, research on the cultivating environment for agricultural products, genetic tests of agricultural products, and so forth. Existing tests are mainly performed by laboratory technicians who have skills for handling reagents. However, the test processes are complex, and a certain skill levels are required to operate the equipment. The μ-TAS technology has been attracting attention as a method having great advantages. The advantages include automatization, increased speed, increased accuracy, cost reduction, promptness, decreased negative effects on the environment, and so forth.

When such an advanced medical test system is generally used, it is necessary that a small amount of a reagent be introduced into a medical testing device used for the medical test system.

In the above-described medical testing devices and other devices having a fine structure, a fine flow passage is arranged to handle a reagent in the structure. However, the order of the amount of the reagent is different from that used in the existing tests. For this reason, it is very difficult to introduce a reagent into such a flow passage.

As PTL 1 discloses, a fluid device having a flat plate structure has an introducing space having a supply port open toward the vertical direction and a fine flow passage extending in a planar direction. The flat shape is utilized to form the flow passage while a direction of the opening and a direction in which the flow passage extends are different by 90 degrees in order to facilitate introduction of a liquid using a pipet or the like and holding of the introduced liquid. In order to receive a liquid from a liquid supply unit such as a pipet and hold the liquid, the introducing space needs to have a size larger than the size of the flow passage. Accordingly, sectional areas on one side and the other of a connecting portion, in which an end portion of the flow passage and the introducing space are connected, are significantly different from each other.

In this portion, air bubbles are easily formed in particular when the liquid is added or replaced, thereby causing various problems in the flow passage device.

In particular, small air bubbles tend to be formed when liquids are mixed. Accordingly, there is a high possibility of introduction of bubbles, that is, a phenomenon in which the bubbles formed are introduced into the flow passage along with the liquid.

In some cases, when a liquid flows in the flow passage along with bubbles in the flow passage of, for example, a heating system, the bubbles may expand and clog the flow passage. In addition, because of the difference in elasticity between fluid and gas, an intended transportation of the liquid is not achieved when a pressure is applied.

The above-described problems are significant problems when a reagent is added or replaced. In particular, in order to cause a reaction in a fine flow passage, a complex operation such as mixing or separating reagents is required. In order to do this, different reagents need to be sequentially introduced into the flow passage. At this time, when a preceding reagent remains in the introducing space, a following reagent is mixed with the preceding reagent. This causes contamination of the reagent. In order to suppress effects caused by the contamination, the remaining amount of a preceding reagent may be decreased and a sufficient amount of a following reagent may be introduced. In this case, however, the above-described phenomenon in which bubbles are introduced is very likely to occur. Since the volume held by the flow passage is small and an interface formed in the connecting portion is easily moved, the interface formed in the connecting portion is easily moved toward the flow passage side by an application of a small amount of force.

CITATION LIST

Patent Literature

PTL 1 Japanese Patent Laid-Open No. 2010-65584

SUMMARY OF INVENTION

Technical Problem

The present invention provides a flow passage device with which a liquid is easily introduced and introduction of air bubbles into a flow passage along with a liquid can be decreased.

Solution to Problem

In order to solve the above-described problems, a flow passage device according to the present invention includes a flow passage through which a fluid flows in a direction crossing a vertical direction, an introducing space that has a supply port opening on an upper surface thereof, the introducing space communicating with an end portion of the flow passage, and a connecting space one end of which is connected to the end portion of the flow passage and the other end of which is connected to the introducing space, the connecting space allowing a gas-liquid interface to be formed due to surface tension, the gas-liquid interface being larger than a section of the flow passage. In the flow passage device, a direction in which the gas-liquid interface faces crosses the vertical direction.

According to the present invention, the direction the interface faces is a direction different from the vertical direction in the connecting space that connects the introducing space to the flow passage. Thus, the flow passage device can be provided, which can be easily fabricated and with which the possibility of air bubbles being introduced into the flow passage along with a liquid when the liquid is introduced into the flow passage can be decreased.

BRIEF DESCRIPTION OF DRAWINGS

FIG. 4A is a side sectional view illustrating a state in which a first liquid is introduced into the flow passage device according to the first embodiment.

FIG. 4B is a top view illustrating the state in which a first liquid is introduced into the flow passage device according to the first embodiment.

FIG. 8 is a flowchart of a method of transporting a liquid according to the present invention.

DESCRIPTION OF EMBODIMENTS

The present invention will be described below with reference to the drawings.

Figure 1A:
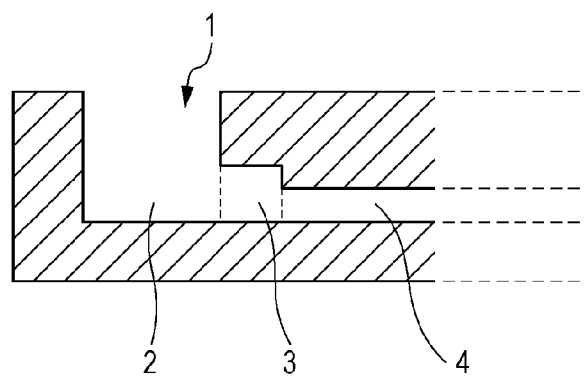
FIG. 1A is a sectional view of a flow passage device according to the present invention.

As illustrated in FIG. 1A, a flow passage device according to the present invention includes a flow passage 4, an introducing space 2, and a connecting space 3. A fluid flows through the flow passage 4 in a direction that crosses the vertical direction. The introducing space 2 has a supply port 1, of which an upper surface is open, and communicates with an end portion of the flow passage 4. The connecting space 3 connects the end portion of the flow passage 4 to the introducing space 2.

Figure 1B:
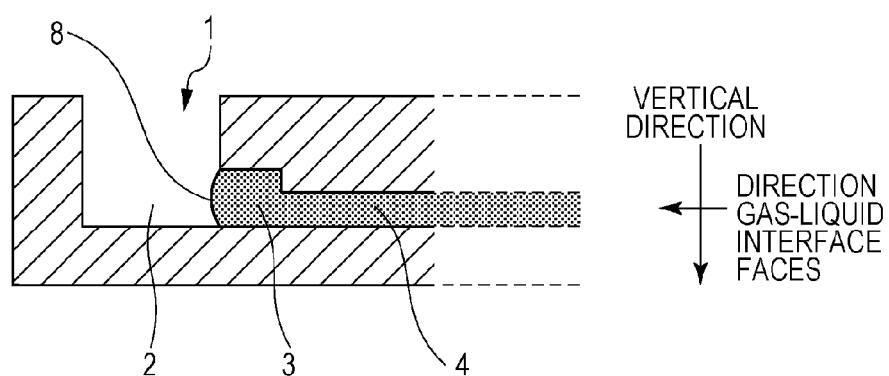
FIG. 1B illustrates a state in which a liquid is held by a flow passage and a connecting space.

The connecting space 3 is formed such that, when a liquid exists in the flow passage 4 as illustrated in FIG. 1B, a gas-liquid interface larger than the section of the flow passage 4 can be formed due to surface tension, and a direction in which the gas-liquid interface faces crosses the vertical direction. In FIG. 1B, a gas-liquid interface (meniscus) 8 is schematically illustrated.

A gas-liquid interface (meniscus) is a curved surface formed due to surface tension of a liquid. In the present invention, as illustrated in FIG. 1B, the surface of the gas-liquid interface 8 is a surface that has boundaries with the gas, liquid, and wall surfaces. The direction in which the gas-liquid interface 8 faces refers to a direction perpendicular to the surface having boundaries with the gas, liquid, and wall surfaces.

The gas-liquid interface 8 in the connecting space 3 is formed when the introducing space 2 is not filled with a liquid. That is, the connecting space 3 has a structure that facilitates formation of an interface due to surface tension of a liquid to hold the liquid.

By doing this, when a reagent is changed, a small amount of a reagent remaining in the connecting space 3 and a target reagent introduced into the introducing space 2 can be mixed. In addition, the liquid to be introduced can be mixed with the remaining reagent at the gas-liquid interface 8 that is larger than the section of the flow passage 4. This substantially prevents bubbles from being introduced into the flow passage 4 along with the liquid. That is, liquid transportation that allows the reagent to be efficiently changed without introduction of bubbles can be realized.

Figure 2A:
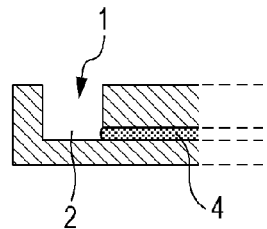
FIGS. 2A to 2C illustrate operations of the related art.
Figure 2D:
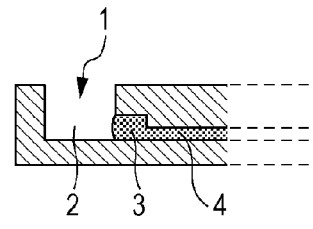
FIGS. 2D to 2F illustrate operations according to the present invention.
Figure 2B:
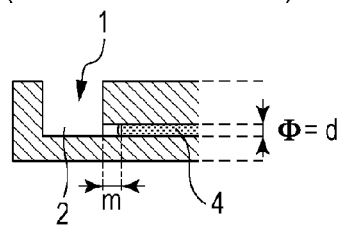
Figure 2E:
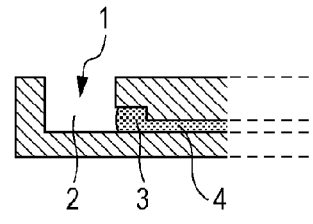
Figure 2C:
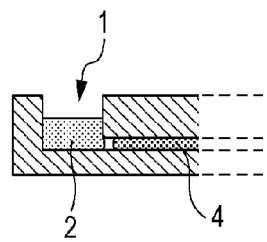
Figure 2F:
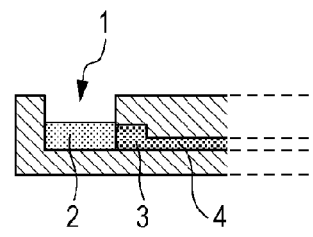

An operation of this liquid transportation will be described in detail with reference to FIGS. 2A to 2F. Out of FIGS. 2A to 2F, FIGS. 2A to 2C illustrate a related-art flow passage device having no connecting space, and FIGS. 2D to 2F illustrate introduction of a liquid using the connecting space 3 according to the present invention. As illustrated in FIGS. 2A to 2C, in a case in which the introducing space 2 is directly connected to the flow passage 4, when no liquid exists in the introducing space 2, a gas-liquid interface 8 is formed in an end portion of the flow passage 4 (FIG. 2A). In this state, when the liquid contracts due to, for example, a decrease in the temperature of the liquid in a central portion of the flow passage 4, the gas-liquid interface 8 is moved toward the flow passage 4 side (FIG. 2B). In a state in which the gas-liquid interface 8 has been moved, when an additional liquid or a replacing liquid is introduced into the introducing space 2, a gas existing in the end portion of the flow passage is introduced into the flow passage 4 along with the liquid, thereby significantly increasing the possibility of air bubbles being formed in a portion where the introducing space 2 is connected to the flow passage 4 (FIG. 2C). That is, when the liquid flows further into the flow passage 4 in this state, a phenomenon in which the liquid flows along with bubbles occurs.

According to the present invention, the connecting space 3 is formed as illustrated in FIGS. 2D to 2F. Thus, even when no liquid exists in the introducing space 2, the connecting space 3 holds a liquid, thereby forming the gas-liquid interface 8 lager than the section of the flow passage 4 (FIG. 2D). The connecting space 3 has a buffering function in a movement of a liquid. Due to this buffering function, the amount of the movement of the gas-liquid interface 8 is very small compared to that of liquid movement in the flow passage 4 (FIG. 2E). Specifically, when the sectional area of the flow passage 4 is d and the movement distance of the gas-liquid interface 8 in the flow passage 4 is m, the volume of the liquid that moves is given by d·m. When the sectional area of the connecting space 3 is s, the movement distance R is given by (d·m)÷s, which will be smaller than m.

When an additional liquid or a replacing liquid is introduced into the introducing space 2 in this state, the liquid introduced can contact the larger gas-liquid interface 8 in the connecting space 3 having a lower obstructing property than that of the end portion of the flow passage 4. Thus, compared to a case illustrated in FIG. 2C, a phenomenon in which bubbles are introduced into the flow passage 4 along with the liquid is suppressed.

In addition, the above-described structure does not need to have a bent flow passage or the like. This simplifies a production process.

To form the gas-liquid interface 8 such that a direction in which the gas-liquid interface 8 faces crosses the vertical direction, the tensions of interfaces between the gas and liquid, the liquid and wall surfaces, and the wall surfaces and gas need to be balanced with each other at the wall surfaces at which the gas-liquid interface 8 is formed. Conditions under which the tensions of the three interfaces are balanced with each other can be adequately adjusted by changing a water repellency of the wall surfaces, the size of the section of the connecting space 3, angles at which the wall surfaces of the connecting space 3 are inclined, and so forth. As the water repellency of the wall surfaces is increased and the size of the section of the connecting space 3 is decreased, the resulting surface tension is increased. As the surface tension is increased, formation of the gas-liquid interface 8 becomes easier.

As illustrated in FIGS. 1A and 1B, in the present invention, the flow passage 4 can extend in a direction the same as the direction in which the gas-liquid interface 8 formed in the connecting space 3 faces. This eliminates a need of arrangement of a complex structure in the end portion of the flow passage 4.

The flow passage device can be formed to have a flat plate shape and the flow passage 4 can extend in a planar direction of the flat plate. This can simplify a production process of the flow passage device.

When the supply port 1, where the upper surface is open, opens toward the vertical direction, a liquid is easily introduced. However, the structure of the supply port 1 is not limited to this.

Bottom surfaces of the introducing space 2, the connecting space 3, and the flow passage 4 can be aligned with each other, and furthermore, can be a single flat substrate. This allows a simplified production process to be used.

The introducing space 2, the connecting space 3, and the flow passage 4 can have heights different from each other in the vertical direction, and the heights in the vertical direction of the introducing space 2, the connecting space 3, and the flow passage 4 can decrease in this order.

The introducing space 2 can be a cylindrically shaped introducing hole, a bottom portion of the introducing hole can be connected to the connecting space 3, and the size of the bottom portion can be larger than the introducing hole so as to form the annular connecting space 3. By doing this, the structure of the flow passage device can be simplified.

A method of transporting a liquid according to the present invention is a method used in a device including the flow passage 4 through which a fluid flows, and the introducing space 2 that has the supply port 1 and communicates with the flow passage 4. The method includes forming of an interface in the connecting space 3 formed between the flow passage 4 and the introducing space 2 due to surface tension of the liquid.

The method can include generating a pressure in the flow passage 4 to move the liquid.

The method can include detecting a state in which the bottom surface of the introducing space 2 has been exposed to stop generation of the pressure in the flow passage 4.

A liquid transportation apparatus with which the flow passage device is used according to the present invention can include a unit arranged to generate a pressure in the flow passage 4 of the flow passage device and a unit arranged to detect a state in which the bottom surface of the introducing space 2 of the flow passage device has been exposed. The unit arranged to detect a state in which the bottom surface has been exposed uses a unit to detect liquid using illumination, or a unit arranged to detect the presence or absence of a liquid using a unit such as a unit arranged to detect electrical resistance in the bottom surface.

The flow passage device according to the present invention is used for a medical testing device. The medical testing devices, a representative example of which are μ-TASs herein, generally refer to devices used in medical tests and diagnoses such as, for example, DNA chips, Labs-on-a-Chip, micro-arrays, protein chips. The medical testing devices are also applicable to the fields of genetic testing, chromosomal testing, cell testing, and the like, biotechnologies, tests of small amounts of substances present in the environment, research on the cultivating environment for agricultural products and the like, genetic tests of agricultural products, and so forth. In the flow passage device according to the present invention, a fine structure including the flow passage can be formed on a substrate.

Embodiments of the present invention will be described in detail below.

First Embodiment

A first embodiment of the present invention will be described.

Figures 3A, 3B:
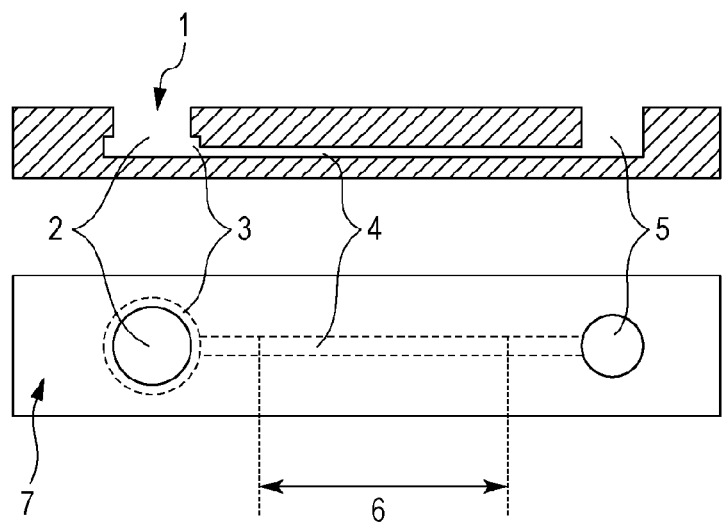
FIG. 3A is a side sectional view of a flow passage device according to a first embodiment.
FIG. 3B is a top view of the flow passage device according to the first embodiment.

FIGS. 3A and 3B illustrate the flow passage device according to the first embodiment. FIG. 3A is a side sectional view of the flow passage device, and FIG. 3B is a top view of the flow passage device. The flow passage is formed in a base material 7, which is made of a flat plate-shaped glass or plastic material. The flow passage device can be molded as a unit, or formed by bonding two or more substrates having a groove of the flow passage to each other.

The flow passage device according to the present invention has flow passage 4 through which a fluid flows formed in the base material 7. The flow passage 4 is defined by a space through which a liquid, a gas, or a semisolid such as a gel-like substance flows. The flow passage 4 has a central portion 6, which is used as a reaction area in which a reacting unit and a detecting unit are arranged. The reacting unit and the detecting unit include a heating unit such as a heater to perform a polymerase chain reaction (PCR) and a light transmitting unit arranged to detect light or to illuminate.

The introducing space 2 that has the supply port 1 opening toward the vertical direction is connected to one of the ends of the flow passage 4. A discharge port 5 is connected to the other end of the flow passage 4. A negative pressure is generated in the flow passage 4 using a pump (not shown) or a syringe (not shown) through the discharge port 5. This allows a reagent and a specimen having been injected into the introducing space 2 to be sucked.

A first liquid is injected into the introducing space 2, which serves as the introducing hole, in an amount sufficient to fill the flow passage 4, and is sucked through the discharge port 5. After the flow passage 4 has been filled with the first liquid, suction of the first liquid through the discharge port 5 is continued.

The step-shaped connecting space 3 is formed at the bottom portion of the introducing space 2 as a introducing bottom area such that the inner diameter of the connecting space 3 is slightly larger than that of the introducing space 2.

As illustrated in FIG. 4A, when the amount of the first liquid contained in the introducing space 2 decreases, the first liquid moves to an peripheral area due to surface tension of the reagent such that the first liquid adheres to a lower periphery portion of the introducing space 2. At the same time, in the connecting space 3, a gas-liquid interface 8 is formed using surface tension. The direction in which the gas-liquid interface 8 faces is a direction that crosses the vertical direction.

Even when the amount of the first liquid decreases to the degree by which the bottom surface of the introducing space 2 is exposed, part of the first liquid is held by the effect of the connecting space 3 and remains around a lower portion of the introducing space 2.

The remaining liquid is sucked into the flow passage 4 due to capillary force of the fine flow passage 4. However, the part of the first liquid that is held in the connecting space 3 is still stably held in the connecting space 3 in a state continuous with the first liquid in the flow passage 4 due to the effect of the surface tension.

Since the remaining amount of the first liquid in the connecting space 3 is smaller than the volume of the introducing space 2, when a second liquid is injected into the introducing space 2 while the bottom surface of the introducing space 2 is exposed, the second liquid is mixed with a small amount of the remaining first liquid in the connecting space 3.

The second liquid having been injected into the introducing space 2 is combined with the first liquid in the introducing space 2 due to the operation of surface tension. Since the gas-liquid interface 8 has a large size, the probability of the first and second liquids being brought into contact with each other is large. Thus, even when bubbles or the like are formed, the formed bubbles are moved through the second liquid from an upper portion of the introducing space 2 to the supply port 1 and removed out of the second liquid.

After the second liquid has been introduced, a negative pressure is again generated in the flow passage 4 to suck the reagent. With a procedure as described above, the first liquid can be replaced with the second liquid.

When the second liquid is introduced, the amount of the first liquid remaining in the introducing space 2 is only the amount of the first liquid remaining in the connecting space 3. Thus, the ratio of the first liquid mixed with the second liquid can be controlled in accordance with the ratio of the volume of the connecting space 3 to the volume of the introducing space 2. The first liquid remains in the connecting space 3, which is a fine groove structure formed around the introducing space 2, due to surface tension. Thus, a liquid to be transported can be changed to the second liquid without introduction of bubbles into the flow passage 4.

The present embodiment can be used for medical tests utilizing a reaction in which the amount of fluorescence in the reagent changes. The reaction is caused by introducing the reagent into the flow passage 4 and continuously applying heat to the reagent in the central portion 6 of the flow passage 4. A unit arranged to continuously apply heat to the reagent includes a heating metal, which, through a protective film, directly contacts the flow passage 4 into which the reagent is introduced. Thus, the reagents can be quickly and stably heated. At the same time, by measuring resistance of platinum which is used with the heater, the temperature of the heating body is detected using a physical constant. By doing this, at what temperature of the reagent a measured amount of fluorescence occurs can be recognized. By introducing different reagents one after another in a medical testing device as described above, different tests can be performed.

According to the gist described in the present embodiment, a small amount of the first liquid remains in an end portion of an opening of the flow passage 4. By doing this, the reagent injected into the introducing space 2 can be substantially completely sucked into the flow passage 4 without bubbles being introduced along with the reagent. At the same time, the amount of the first liquid remaining in the end portion of the opening of the flow passage 4 is sufficiently small compared to the amount of the second liquid injected into the introducing space 2. Thus, the ratio of the first liquid mixed with the second liquid can be decreased, and the amount of the reagent to be mixed can be controlled. When it is known in advance that the first liquid in an amount not exceeding a certain amount can be mixed with the second liquid without affecting the reaction of the second liquid, the volumes of the connecting space 3 and the end portion of the opening of the flow passage 4 can be set to values in the design such that the amount of the first liquid to be mixed with the second liquid does not exceed the certain amount that does not affect the reaction of the second liquid. By doing this, the first liquid can be replaced with the second liquid while the amount of the first liquid to be mixed does not exceed a desired amount.

The first liquid and the second liquid in the present embodiment can be agents or specimens, or liquids such as buffer solutions that are not used for causing reactions. The first liquid and the second liquid can be the same liquids, or liquids different from each other.

Second Embodiment

A second embodiment of the present invention will be described. In the first embodiment, as illustrated in FIG. 3B, the connecting space 3 is formed by extending the bottom surface of the introducing space 2 so as to form a concentric circle. Because of the effect of the connecting space 3, a small space is formed to allow a small amount of the reagent to be held.

In the second embodiment, the connecting space 3 is not formed in a concentric manner. Instead, the connecting space 3 is formed only in the end portion of the opening of the flow passage 4. With the present embodiment, a task of replacing a reagent with the next reagent can be achieved without bubbles being introduced along with the reagent. In addition, the ratio of the first liquid to be mixed with the second liquid can be further decreased.

Figures 5A, 5B:
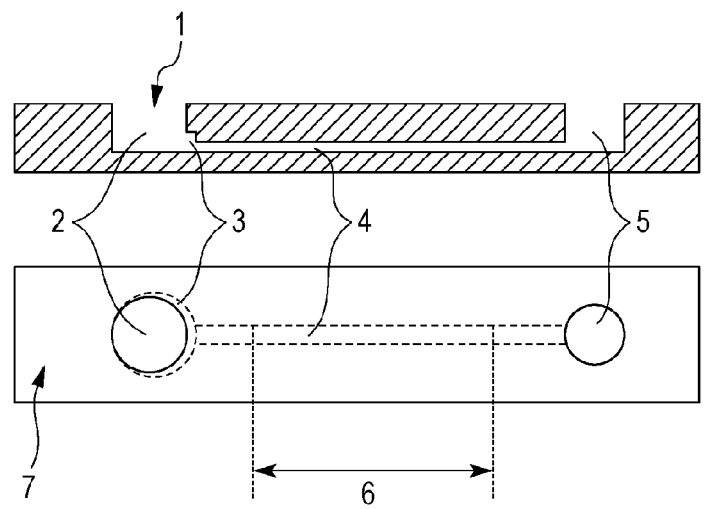
FIG. 5A is a side sectional view of a flow passage device according to a second embodiment.
FIG. 5B is a top view of the flow passage device according to the second embodiment.

In order to do this, as illustrated in FIG. 5B, an inner circle of the connecting space 3 is eccentric with an inner circle of the introducing space 2 instead of concentric to form the connecting space 3. In this case, the volume of the connecting space 3, which forms the groove structure, is smaller compared to the case in which the connecting space 3 is formed in the entire peripheral area of the bottom portion of the introducing space 2. Thus, the amount of the first liquid can be smaller, thereby decreasing the ratio of the first liquid to be mixed.

Third Embodiment

A third embodiment, in which the flow passage device is used for a medical testing device, will be described.

In the third embodiment, as is the case with the first embodiment, the flow passage device illustrated in FIGS. 3A and 3B is used, and the reagent is introduced into the flow passage 4.

The reagent in the flow passage 4 is continuously heated in the central portion 6 of the flow passage 4, thereby causing a reaction in which the fluorescence amount in the reagent changes. This reaction is utilized.

As is the case with the first embodiment, a negative pressure is initially generated in the flow passage 4 using a pump (not shown) or a syringe (not shown) through the discharge port 5. The reagent and the specimen injected into the introducing space 2 are moved to the central portion 6 by controlling the pressure.

In so doing, dye or fluorescence dye can be introduced to make the reagent be visible, so that the pressure can be controlled while the state of the reagent in the flow passage 4 being monitored. As a result, a desired amount of the reagent is sucked to a desired position.

Next, the reagent is heated or cooled using the heater provided in the central portion 6 to cause a reaction.

Reactions caused by heating or cooling include a PCR, thermal melting, a hybridization reaction, an enzymatic reaction, and so forth.

The result of the reaction is detected by a detecting unit.

A detecting unit that performs optical or electrical detection is provided to detect the reaction. In a case of optical detection, fluorescence detection or chemiluminescence detection can be used. In this case, a reagent such as an intercalator, of which the fluorescent brightness changes as a result of the reaction, can be used.

When the first and second liquids are sequentially injected into the flow passage 4, a plurality of reagents are arranged at positions different from each other in the flow passage 4. When the positional relationship of the reagents is monitored while the reagents flow in the flow passage 4, reactions of a plurality of the reagents can be simultaneously observed.

The state of the reagent can be monitored, and feedback information of control of pump can be obtained with respect to monitored behavior of the reagents. This allows a desired amount of the reagent to be arranged and the reagent to be arranged at a desired position.

When the flow passage device according to the present invention is used, a reagent can be introduced while suppressing occurrence of a situation in which the reagent is mixed with another reagent or bubbles are introduced into the fine flow passage 4 along with the reagent. Thus, the flow passage device according to the present invention can be used in detecting the above-described reactions.

Other Embodiments

The introducing space 2 has a circular shape in the first and second embodiments. However, the introducing space 2 does not necessarily have a circular shape. The connecting space 3 does not necessarily have a circular shape, either. Furthermore, the connecting space 3 is not necessarily formed to have a shape similar to the introducing space 2.

In the above-described embodiments, the supply port 1 is open toward the vertical direction. However, the supply port 1 is not necessarily open toward the vertical direction as long as an opening is formed in the upper surface of the introducing space 2. That is, the supply port 1 can be a supply port opening in a plane inclined relative to the horizontal plane.

The direction in which the gas-liquid interface 8 formed in the connecting space 3 faces is not necessarily the horizontal direction as long as the direction in which the gas-liquid interface 8 faces is a direction that crosses the vertical direction. A liquid surface can be inclined relative to the horizontal plane by N degrees. An inclination of N degrees can be adequately set in a range, for example, between 30 degrees to 90 degrees (horizontal direction).

Figure 6A:
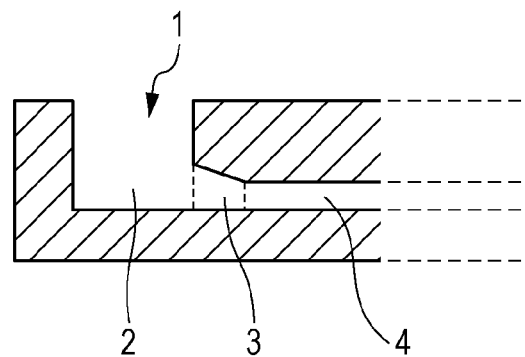
FIGS. 6A to 6C illustrate another embodiments of a connecting space according to the present invention.
Figure 6B:
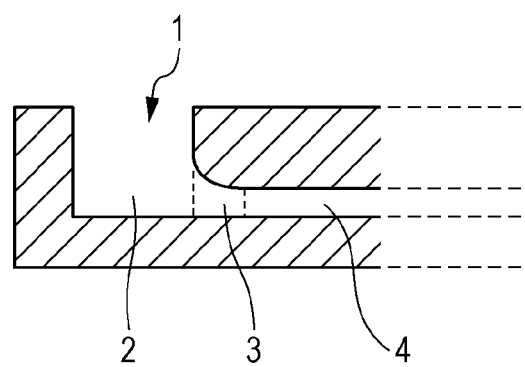
Figure 6C:
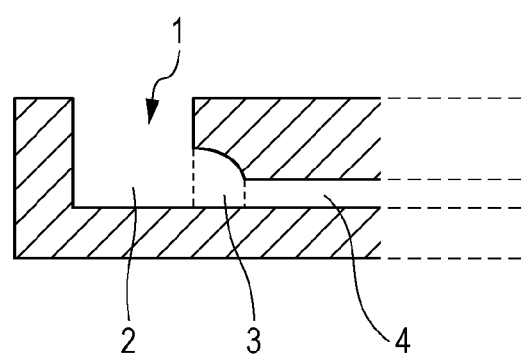

As illustrated in FIGS. 6A to 6C, the sectional shape of the connecting space 3 can be changed relative to a direction in which the connecting space 3 is connected to the introducing space 2. The shapes are so-called tapered shapes that include a linearly inclined shape illustrated in FIG. 6A, a downwardly convex curved shape in FIG. 6B, and an upwardly convex curved shape in FIG. 6C. When wall surfaces of these shapes are set to be higher on the introducing space 2 side so as to allow air bubbles having been formed to move up toward the opening side, a situation in which air bubbles remain can be more avoidable.

Apparatus Configuration Using Flow Passage Device

An apparatus using the flow passage device according to the above-described embodiments and a method of transporting a liquid will be described in detail below.

Figure 7:
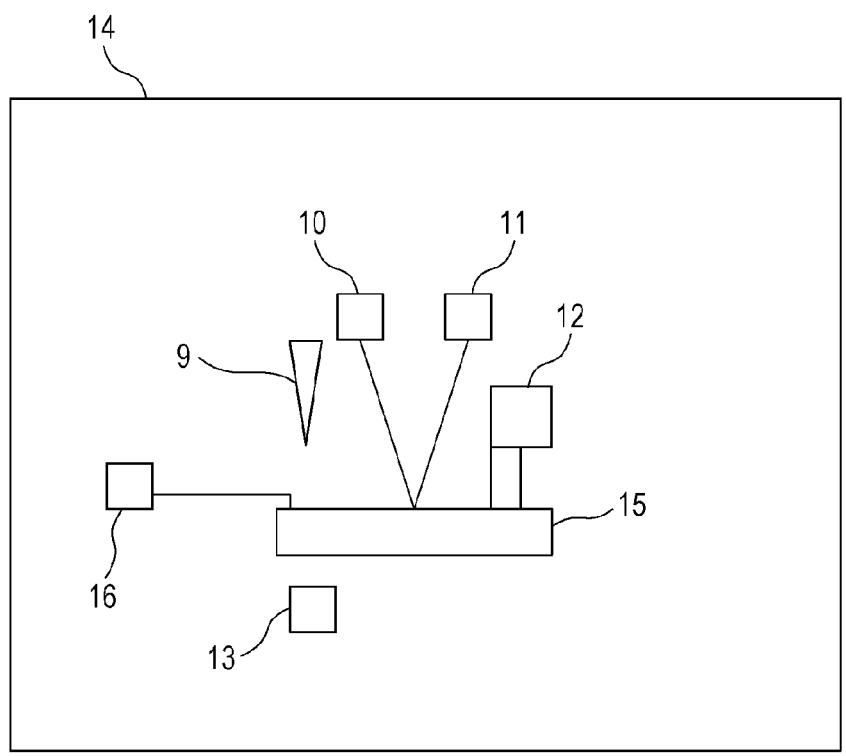
FIG. 7 illustrates a configuration of a liquid transportation apparatus according to the present invention.

FIG. 7 illustrates a configuration of the liquid transportation apparatus according to the present invention.

A liquid transportation apparatus 14 includes a pressure unit 12 that generates a positive or negative pressure in the flow passage 4 of the flow passage device and a liquid detection unit 13 that detects a state in which the bottom surface of the introducing space 2 of the flow passage device has been exposed. The pressure unit 12 uses a pump unit such as a syringe pump that is connected to the discharge port 5 of a flow passage device 15 to generate a pressure in the flow passage 4. The liquid detection unit 13 can use a unit that detects the presence or absence of a liquid using an optical unit that detects reflection of the bottom surface or an electrical unit such as a resistor.

Reference numeral 9 denotes a liquid introducing unit such as a pipet and reference numeral 15 denotes the flow passage device.

Reference numerals 10 and 11 respectively denote a light emitting unit such as a laser and a light detecting unit such as a CCD sensor. The light emitting unit 10 and the light detecting unit 11 are included in a reaction detection unit. In addition, the liquid transportation apparatus 14 includes a receiving unit (not shown) by which the flow passage device 15 is received, a power source 16 to which a heater member provided in the flow passage device 15 and the like are electrically connected, and so forth. The liquid transportation apparatus 14 can also include a control unit (computer) therein that controls the above-described components.

FIG. 8 is a flowchart of a method of transporting a liquid using the above-described liquid transportation apparatus 14.

The flow passage device 15, which has the flow passage 4 and the introducing space 2, is initially prepared. A fluid flows through the flow passage 4. The introducing space 2 has the supply port 1 and communicates with the flow passage 4.

Next, the flow passage device 15 is set in the receiving unit of the liquid transportation apparatus 14. Then, the first liquid is introduced into the introducing space 2 of the flow passage device 15 using the liquid introducing unit 9.

After that, a pressure difference is applied in the flow passage 4 using the pressure unit 12, thereby introducing the first liquid held in the introducing space 2 into the flow passage 4 through the connecting space 3.

When the remaining first liquid has been substantially removed from the introducing space 2 as a result of continued introduction of the first liquid held in the introducing space 2 into the flow passage 4, the gas-liquid interface 8 is formed in the connecting space 3 due to the surface tension of the first liquid. The gas-liquid interface 8 has a surface that faces a direction crossing the vertical direction. When introduction of the first liquid into the flow passage 4 is further continued, the first liquid is completely removed from the connecting space 3, and there is no longer the gas-liquid interface 8.

However, when a state in which the bottom surface of the introducing space 2 has been exposed is detected using the liquid detection unit 13, and generation of a pressure in the flow passage 4 is stopped, a state before the gas-liquid interface 8 is removed, that is, a state in which the gas-liquid interface 8 is still present in the connecting space 3 can be detected.

When the second liquid is introduced into the introducing space 2 to replace the first liquid or to increase the amount of the first liquid, the second liquid is introduced into the introducing space 2 while the gas-liquid interface 8 is present in the connecting space 3.

Then, a pressure difference is again applied in the flow passage 4 using the pressure unit 12, thereby introducing the second liquid held in the introducing space 2 into the flow passage 4.

Power is supplied from the power source 16 to the heater member of the flow passage device 15 to control the temperature of the introduced liquid in the flow passage 4. The temperature control includes, for example, application of a temperature cycle for PCR and heating for measurement of thermal melting.

Along with the temperature control, or after the temperature control, a reaction in the flow passage 4 is detected using the reaction detection unit. As a result of the detection, the presence or absence of the reaction or the amount of the reaction can be determined, and accordingly, the reaction in the flow passage 4 can be analyzed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-031039, filed Feb. 16, 2011, which is hereby incorporated by reference herein in its entirety.

REFERENCE SIGNS LIST 1 supply port
2 introducing space
3 connecting space
4 flow passage
5 discharge port
6 central portion
7 base material

The invention claimed is:
1. A flow passage device comprising:
a flow passage through which a fluid flows in a direction crossing a vertical direction;
an introducing space that has a supply port opening on an upper surface thereof and that has a bottom surface, the introducing space communicating with an end portion of the flow passage; and
a connecting space one end of which is connected to the end portion of the flow passage and the other end of which is connected to the introducing space, the connecting space having a bottom surface, the connecting space allowing a gas-liquid interface to be formed due to surface tension, the gas-liquid interface being larger than a section of the flow passage,
wherein a direction in which the gas-liquid interface faces crosses the vertical direction,
wherein a part of a side of a bottom portion of the introducing space is open and connected to the connecting space,
wherein the bottom surface of the introducing space and the bottom surface of the connecting space are on a single flat surface, and the introducing space is not narrowed from the bottom surface to the supply port opening,
wherein neither a length, in the same axis as that of the flow passage, of the introducing space nor a width of the introducing space is narrowed,
wherein the direction in which the gas-liquid interface faces is the vertical direction in a case where a liquid surface of a liquid in the introducing space is situated higher than an upper surface of the connecting space, and
wherein, in a case where the liquid in the introducing space decreases and the bottom surface of the introducing space is exposed, the liquid, due to surface tension of the liquid, moves such that the liquid adheres to a lower periphery portion of the introducing space while the gas-liquid interface is formed, in a direction crossing the vertical direction, between the upper surface and a bottom surface of the connecting space.

2. The flow passage device according to claim 1, wherein the flow passage extends in a direction the same as a direction in which the gas-liquid interface formed in the connecting space faces.

3. The flow passage device according to claim 1, wherein the flow passage device has a flat plate shape, wherein the flow passage extends in a planar direction of the flat plate.

4. A flow passage device according comprising:
a flow passage through which a fluid flows in a direction crossing a vertical direction;
an introducing space that has a supply port opening on an upper surface thereof and that has a bottom surface, the introducing space communicating with an end portion of the flow passage; and
a connecting space one end of which is connected to the end portion of the flow passage and the other end of which is connected to the introducing space, the connecting space having a bottom surface, the connecting space allowing a gas-liquid interface to be formed due to surface tension, the gas-liquid interface being larger than a section of the flow passage,
wherein a direction in which the gas-liquid interface faces crosses the vertical direction,
wherein the introducing space is a cylindrically shaped introducing hole,
wherein a bottom portion of the introducing hole is connected to the connecting space,
wherein the connecting space is a form of annular connecting space,
wherein the bottom surface of the introducing space and the bottom surface of the connecting space are on a single flat surface, and the introducing space is not narrowed from the bottom surface to the supply port opening,
wherein neither a length, in the same axis as that of the flow passage, of the introducing space nor a width of the introducing space is narrowed,
wherein the direction in which the gas-liquid interface faces is the vertical direction in a case where a liquid surface of a liquid in the introducing space is situated higher than an upper surface of the connecting space, and
wherein, in a case where the liquid in the introducing space decreases and the bottom surface of the introducing space is exposed, the liquid, due to surface tension of the liquid, moves such that the liquid adheres to a lower periphery portion of the introducing space while the gas-liquid interface is formed, in a direction crossing the vertical direction, between the upper surface and a bottom surface of the connecting space.

5. The flow passage device according to claim 1, wherein the introducing space, the connecting space, and the flow passage have heights different from each other in the vertical direction.

6. The flow passage device according to claim 5, wherein the heights in the vertical direction of the introducing space, connecting space, and the flow passage decrease in this order.

7. A method of transporting a liquid in a device including a flow passage through which a fluid flows, an introducing space that has a supply port and communicates with the flow passage and that has a bottom surface, and a connecting space formed between the flow passage and the introducing space, the connecting space having a bottom surface, the method comprising:
forming a gas-liquid interface in the connecting space formed between the flow passage and the introducing space due to surface tension of the liquid, the gas-liquid interface having a surface that faces a direction crossing the vertical direction,
wherein a part of a side of a bottom portion of the introducing space is open and connected to the connecting space,
wherein the bottom surface of the introducing space and the bottom surface of the connecting space are on a single flat surface, and the introducing space is not narrowed from the bottom surface to the supply port opening,
wherein neither a length, in the same axis as that of the flow passage, of the introducing space nor a width of the introducing space is narrowed,
wherein the direction in which the gas-liquid interface faces is the vertical direction in a case where a liquid surface of a liquid in the introducing space is situated higher than an upper surface of the connecting space, and
wherein, in a case where the liquid in the introducing space decreases and the bottom surface of the introducing space is exposed, the liquid, due to surface tension of the liquid, moves such that the liquid adheres to a lower periphery portion of the introducing space while the gas-liquid interface is formed, in a direction crossing the vertical direction, between the upper surface and a bottom surface of the connecting space.

8. The method of transporting a liquid according to claim 7, further comprising:
generating a negative pressure or a positive pressure in the flow passage to move a liquid.

9. The method of transporting a liquid according to claim 8, further comprising:
detecting a state in which a bottom surface of the introducing space has been exposed to stop generation of the pressure in the flow passage.

10. A liquid transportation apparatus comprising:
a unit arranged to generate a positive pressure or a negative pressure in the flow passage of the flow passage device according to claim 1; and
a unit arranged to detect a liquid in order to detect a state in which a bottom surface of the introducing space of the flow passage device has been exposed.

11. The flow passage device according to claim 1, wherein the introducing space is a cylindrically shaped introducing hole.

12. The flow passage device according to claim 1, wherein a bottom surface of the introducing space, a bottom surface of the connecting space, and a bottom surface of the flow passage are located at a same height.

13. A flow passage device comprising:
a flow passage through which a fluid flows in a direction crossing a vertical direction; an introducing space that has a supply port opening on an upper surface thereof and that has a bottom surface, the introducing space communicating with an end portion of the flow passage; and
a connecting space one end of which is connected to the end portion of the flow passage and the other end of which is connected to the introducing space, the connecting space having a bottom surface, the connecting space being larger than a section of the flow passage,
wherein a part of a side of a bottom portion of the introducing space is open and connected to the connecting space,
wherein the bottom surface of the introducing space and the bottom surface of the connecting space are on a single flat surface, and the introducing space is not narrowed from the bottom surface to the supply port opening,
wherein neither a length, in the same axis as that of the flow passage, of the introducing space nor a width of the introducing space is narrowed,
wherein the direction in which the gas-liquid interface faces is the vertical direction in a case where a liquid surface of a liquid in the introducing space is situated higher than an upper surface of the connecting space, and
wherein, in a case where the liquid in the introducing space decreases and the bottom surface of the introducing space is exposed, the liquid, due to surface tension of the liquid, moves such that the liquid adheres to a lower periphery portion of the introducing space while the gas-liquid interface is formed, in a direction crossing the vertical direction, between the upper surface and a bottom surface of the connecting space.

* * * * *